United States Patent [19]

Crowe

[11] Patent Number: 5,814,193

[45] Date of Patent: Sep. 29, 1998

[54] PROCESS FOR THE PURIFICATION OF A $C_2$ TO $C_4$ CARBOXYLIC ACID AND/OR ANHYDRIDE HAVING HALIDE IMPURITIES

[75] Inventor: Barry Crowe, Sutton-on-Hull, England

[73] Assignee: BP Chemicals Limited, London, England

[21] Appl. No.: 695,273

[22] Filed: Aug. 9, 1996

[30] Foreign Application Priority Data

Aug. 17, 1995 [GB] United Kingdom .................. 9516892
Feb. 21, 1996 [GB] United Kingdom .................. 9603611

[51] Int. Cl.$^6$ .............................. C07C 51/00; C07C 1/00; C07C 51/42
[52] U.S. Cl. .................................. 204/157.87; 204/157.6; 204/158.2; 204/158.21; 562/497; 562/520; 562/517; 562/608
[58] Field of Search .............................. 204/157.4, 157.6, 204/157.87, 158.2, 158.21; 562/497, 520, 517, 608

[56] References Cited

U.S. PATENT DOCUMENTS

| 1,679,256 | 7/1928 | Müller et al. ...................... | 204/158.21 |
| 2,149,765 | 3/1939 | Goos et al. .............................. | 260/540 |
| 4,171,251 | 10/1979 | Fowler ................................. | 204/158 R |
| 4,268,362 | 5/1981 | Ogawa et al. .......................... | 562/608 |
| 5,202,481 | 4/1993 | Scates et al. ............................ | 562/517 |
| 5,358,611 | 10/1994 | Bauer, Jr. et al. ............... | 204/157.093 |

FOREIGN PATENT DOCUMENTS

| 40 16 514 A1 | 11/1991 | Germany . |
| 41 32 672 A1 | 4/1993 | Germany . |
| 56-18932 | 2/1981 | Japan . |
| 6-15492 | 3/1994 | Japan . |

OTHER PUBLICATIONS

"Removal of Iodoorganic Compounds from Kerosene in Nuclear Fuel Reprocessing"; *J. Radioanal. Nucl. Chem. Letters*; O. Kindel et al.; No. 176 (3), pp. 251–259; ©1993.

Primary Examiner—Kathryn L. Gorgos
Assistant Examiner—Edna Wong
Attorney, Agent, or Firm—Fay, Sharpe, Beall, Fagan, Minnich & McKee

[57] ABSTRACT

A process for the purification of a $C_2$ to $C_4$ carboxylic acid and/or an anhydride thereof having halide impurities, which process comprises the steps of (a) exposing the impure acid and/or anhydride to electromagnetic radiation under conditions of intensity, wavelength and temperature, and for a time, sufficient to convert at least a portion of the halide impurities to lower—and/or higher-boiling halide components and (b) separating the lower—and/or higher-boiling halide components formed in step (a) from the $C_2$ to $C_4$ carboxylic acid and/or anhydride. Also, a process for the purification of a $C_2$ to $C_4$ carboxylic acid and/or anhydride thereof prepared by a carbonylation process, the acid and/or anhydride thereof having a non-halide, non-acidic and/or non-anhydride impurities, which process comprises the steps of (a) exposing the impure acid and/or anhydride to electromagnetic radiation under conditions of intensity, wavelength and temperature, and for a time, sufficient to convert at least a portion of the non-halide, non-acidic and/or non-anhydride impurities to lower-and/or higher-boiling non-halide, non-acidic and/or non-anhydride components and (b) separating the lower-and/or higher-boiling non-halide, non-acidic and/or non-anhydride components formed in step (a) from the $C_2$ to $C_4$ carboxylic acid and/or anhydride.

14 Claims, 7 Drawing Sheets

PROCESS FOR THE PURIFICATION OF A $C_2$ TO $C_4$ CARBOXYLIC ACID AND/OR ANHYDRIDE HAVING HALIDE IMPURITIES

BACKGROUND OF THE INVENTION

The present invention relates to a purification process and in particular to a process for the purification of a $C_2$ to $C_4$ carboxylic acid and/or anhydride thereof having halide impurities.

Carboxylic acids and their anhydrides may be manufactured by a variety of processes. For example acetic acid may be manufactured by the oxidation of hydrocarbons such as ethane, butane and naphtha. Acetic acid and its corresponding anhydride may be manufactured by carbonylation, for example, carbonylation of methanol to acetic acid as described in UK Patents GB 1233121 and GB 1234641. The co-production of acetic acid and acetic anhydride by carbonylation is described in European patent application EP-A-0087870. Acetic anhydride may also be manufactured by absorbing ketene into acetic acid.

The carboxylic acids and corresponding anhydrides manufactured by known methods are generally purified by one or more distillation stages. However, even after such purification the acid and/or anhydride products often contain small amounts of non-acidic and/or non-anhydride impurities. The nature of these impurities depends upon the process of manufacture used but may comprise ketones and esters, and where carbonylation manufacturing processes are used, may also comprise halide-containing compounds such as organic and inorganic iodides.

Methods are known for removing impurities from carboxylic acids and/or anhydrides. Thus, for example, UK patent GB 1293774 describes a process for removing a halide impurity from a carboxylic acid by treatment with an inorganic oxidising compound followed by distillative separation. UK patent GB 749098 describes a process for purifying acetic anhydride by treatment with hydrogen peroxide or peracetic acid.

However, none of these processes is entirely satisfactory.

The use of light, such as UV light, in purification processes is known.

Thus, JP-56-18932 describes a method of improving the quality of acetic acid, containing impurities such as alcohols, aldehydes, ketones, carboxylic acids and esters, particularly its quality as based on the 'acid wash colour test' by irradiating the acetic acid with light.

JP-94-15492 relates to a method of refining acetic anhydride containing diketene impurities in which the crude acetic anhydride is processed by irradiation with UV rays and distilled as necessary either simultaneously with or after said processing.

J. Radioanal. Nucl. Chem., Letters 176(3) 251–259 (1993) relates to removal of iodoorganic compounds from kerosene in nuclear fuel reprocessing. Decomposition of iodododecane in n-dodecane solution to elemental iodine is said to be achieved by exposure to a high intensity UV-light.

SUMMARY OF THE INVENTION

Thus, according to the present invention there is provided a process for the purification of a $C_2$ to $C_4$ carboxylic acid and/or an anhydride thereof having halide impurities, which process comprises the steps of (a) exposing the impure acid and/or anhydride to electromagnetic radiation under conditions of intensity, wavelength and temperature, and for a time, sufficient to convert at least a portion of the halide impurities to lower—and/or higher-boiling halide components and (b) separating the lower—and/or higher-boiling halide components formed in step (a) from the $C_2$ to $C_4$ carboxylic acid and/or anhydride.

The process of the present invention may be used for the purification of acetic acid, propionic acid, n-butyric acid, isobutyric acid and mixtures thereof. The process of the present invention may be used for the purification of anhydrides, mixed anhydrides and mixtures of one or more thereof with acetic acid, propionic acid, n-butyric acid and iso-butyric acid. Mixtures of carboxylic acids and anhydrides may be used. Preferably the process of the present invention is used for the purification of acetic acid. Preferably, the acetic acid is prepared by the carbonylation of methanol, for example as described in UK patents GB 1233121 and GB 1234641 and/or by the carbonylation of methanol and/or methyl acetate for example as described in European Patent application EP-A-0087870, and/or by the carbonylation of dimethylether.

Preferably, the halide impurities are iodine-containing compounds, such as organic and/or inorganic iodides. More preferably the halide impurities are organic $C_5$ to $C_7$ iodides. The concentration of organic $C_5$ to $C_7$ iodides in the impure $C_2$ to $C_4$ carboxylic acid and/or anhydride thereof is typically in the range 10 ppb to 10 ppm.

In a further embodiment of the process of the present invention there is provided a process for the purification of a $C_2$ to $C_4$ carboxylic acid and/or an anhydride thereof having $C_5$ to $C_7$ iodide impurities, which process comprises the steps of (a) exposing the impure acid and/or anhydride to electromagnetic radiation under conditions of intensity, wavelength and temperature, and for a time, sufficient to convert a least a portion of the $C_5$ to $C_7$ iodide impurities to methyl iodide and (b) separating the methyl iodide formed in step (a) from the $C_2$ to $C_4$ carboxylic acid and/or anhydride.

The $C_2$ to $C_4$ carboxylic acid and/or anhydride thereof may also have non-halide, non-acidic and/or non-anhydride impurities such as $C_1$ to $C_6$ ketones and/or $C_1$ to $C_4$ esters and/or mesityl oxide which may be present at any level, but for example, the non-halide, non-acidic and/or non-anhydride impurities are typically in the range 2 to 200 ppm.

The non-halide, non-acidic and/or non-anhydride impurities, if present, are believed to be converted to lower and/or higher-boiling non-halide, non-acidic and/or non-anhydride components which may be separated by distillation. It is believed that the non-halide, non-acidic and/or non-anhydride impurities are converted to higher-boiling non-halide components by oligomerisation of ketones and esters. It may be possible to reduce the non-halide, non-acidic and/or non-anhydride impurities by 90% within 90 mins.

The presence of oxidisable non-halide, non-acidic and/or non-anhydride impurities may result in unacceptably low permanganate times as hereindefined. It has been found that the electromagnetic radiation treatment process of the present invention increases the permanganate time of acetic acid and that the permanganate time is further increased after separation in step (b) of the process.

The process of the present invention may be operated as a batch or continuous process, preferably a continuous process.

The impure carboxylic acid and/or anhydride may be exposed to the radiation in step (a) as a solution in a suitable solvent but is preferably exposed as neat, undiluted material.

The impure carboxylic acid and/or anhydride may be exposed to the electromagnetic radiation as a vapour or liquid.

The impure carboxylic acid and/or anhydride may be exposed to the electromagnetic radiation in step (a) at any suitable pressure. Step (a) should be performed at a temperature which is sufficiently elevated to prevent the impure acid and/or anhydride freezing. Higher temperatures reduce the time necessary for exposure of the impure acid and/or anhydride, but if the temperature is too high the efficiency of the irradiating source may be reduced. A suitable operating temperature is from 20° to 85° C.

Suitable sources of electromagnetic radiation are medium pressure and low pressure mercury lamps. Such lamps emit radiation predominantly in the wavelength ranges 300 to 370 nm and 254 nm respectively and may have a power output up to 2 kilowatt, preferably up to 250 watts. More than one lamp may be used depending upon the power of the lamp and the amount of impure acid and/or anhydride to be treated. For example up to several thousand lamps may be used on an industrial scale. The impure acid and/or anhydride is exposed to the radiation for sufficient time to convert the halide impurities to lower—and/or higher-boiling halide components. By lower-boiling halide components is meant halide compounds having a lower boiling point than the halide impurities. By higher-boiling halide components is meant halide compounds having a higher boiling point than the halide impurities. The halide impurities are believed to be converted to halide compounds, for example, methyl iodide, which may be separated from the acid and/or anhydride. The time of exposure will depend upon, amongst other things, the concentration of impurities, the wavelength and intensity of the radiation, the temperature and the like. Generally the time of exposure will be up to about 10 hours, preferably up to about 5 hours, more preferably up to about 3 hours. It may be possible to reduce organic $C_5$ to $C_7$ iodides by 90% within 30 minutes.

In step (b) the lower—and/or higher-boiling halide components and, if formed, the higher-boiling non-halide residues are separated from the carboxylic acid and/or anhydride thereof by any suitable means, for example by distillation, or by semi-permeable membrane filtration, and the like, preferably by distillation. The lower-boiling halide components may have a sufficiently low boiling point that flash distillation may be used to effect the separation. The higher-boiling halide and non-halide residues may have a sufficiently higher boiling point to that of the purified acid and/or anhydride that flash distillation may be used to effect the separation. Preferably, fractional distillation with heads and tail bleeds is used for the separation(s), for example, a column with head take off to remove low-boiling iodides, sides take off to remove purified acetic acid and/or anhydride and base take off to remove high-boiling residues.

Preferably the concentration of total iodides in the product acid is less than 10 ppb and for the product anhydride is less than 1 ppm.

The exposure and separation steps may be performed concurrently, for example by exposing impure acid and/or anhydride in a section of a distillation column provided that residence times are sufficient, or preferably is performed sequentially by exposing the impure acid and/or anhydride in a separate vessel prior to distillative separation.

DESCRIPTION OF THE PREFERRED EMBODIMENTS

Figure 1:
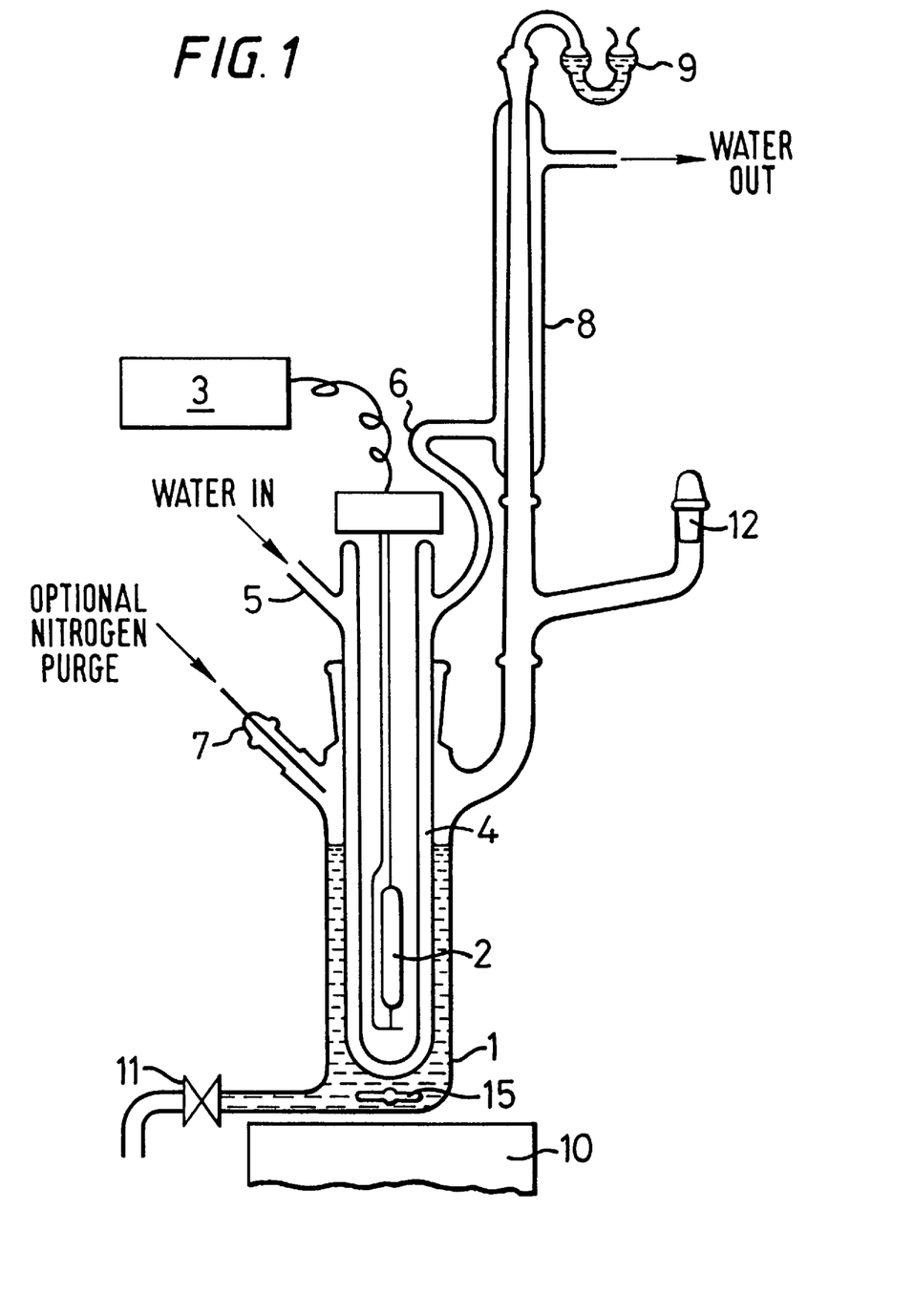
FIG. 1 is a diagrammatic representation of the apparatus in which the inventive process is performed.
Figure 2:
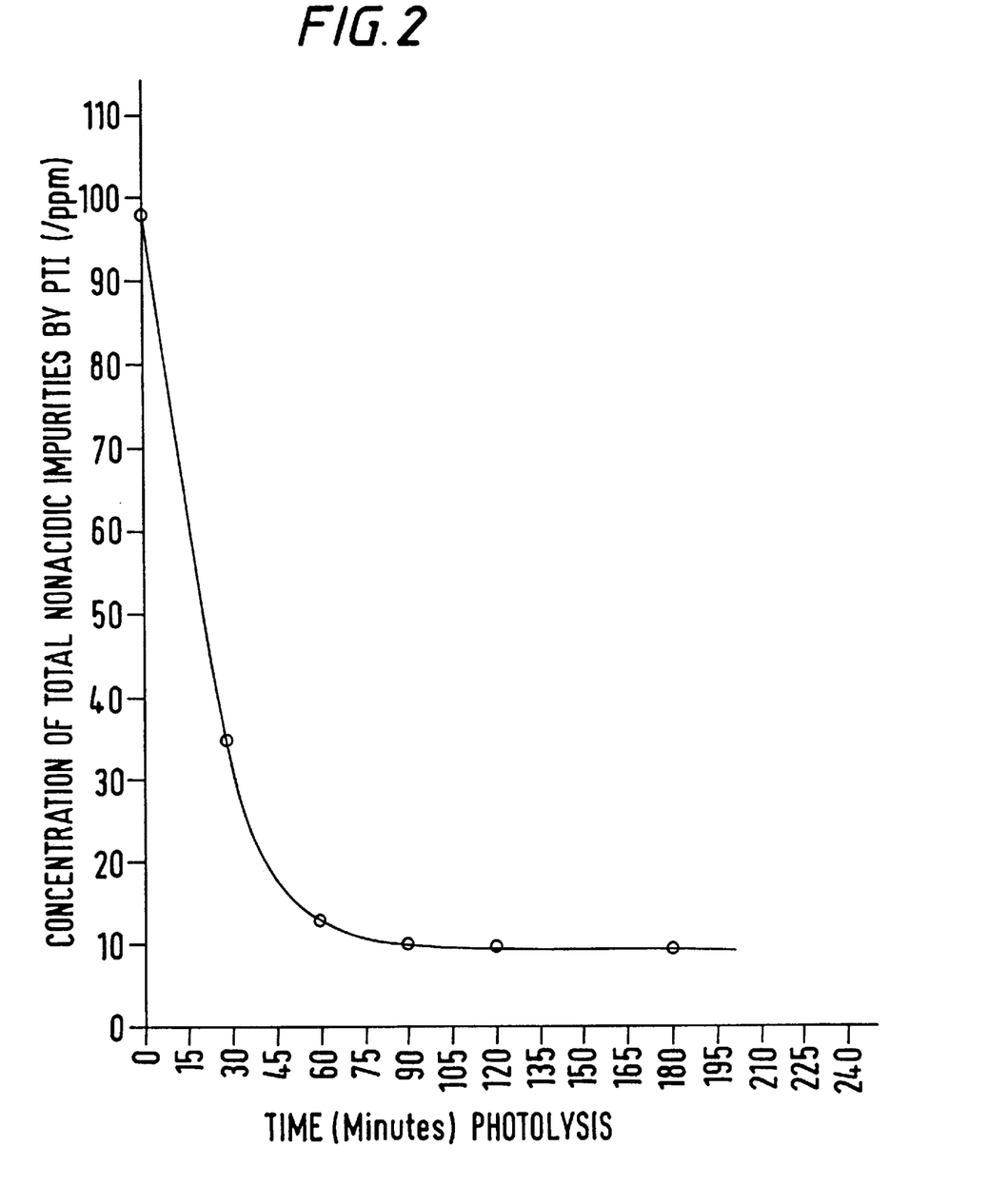
FIG. 2 is a graphical representation of the concentration of total non-acidics of Example 1.
Figure 3:
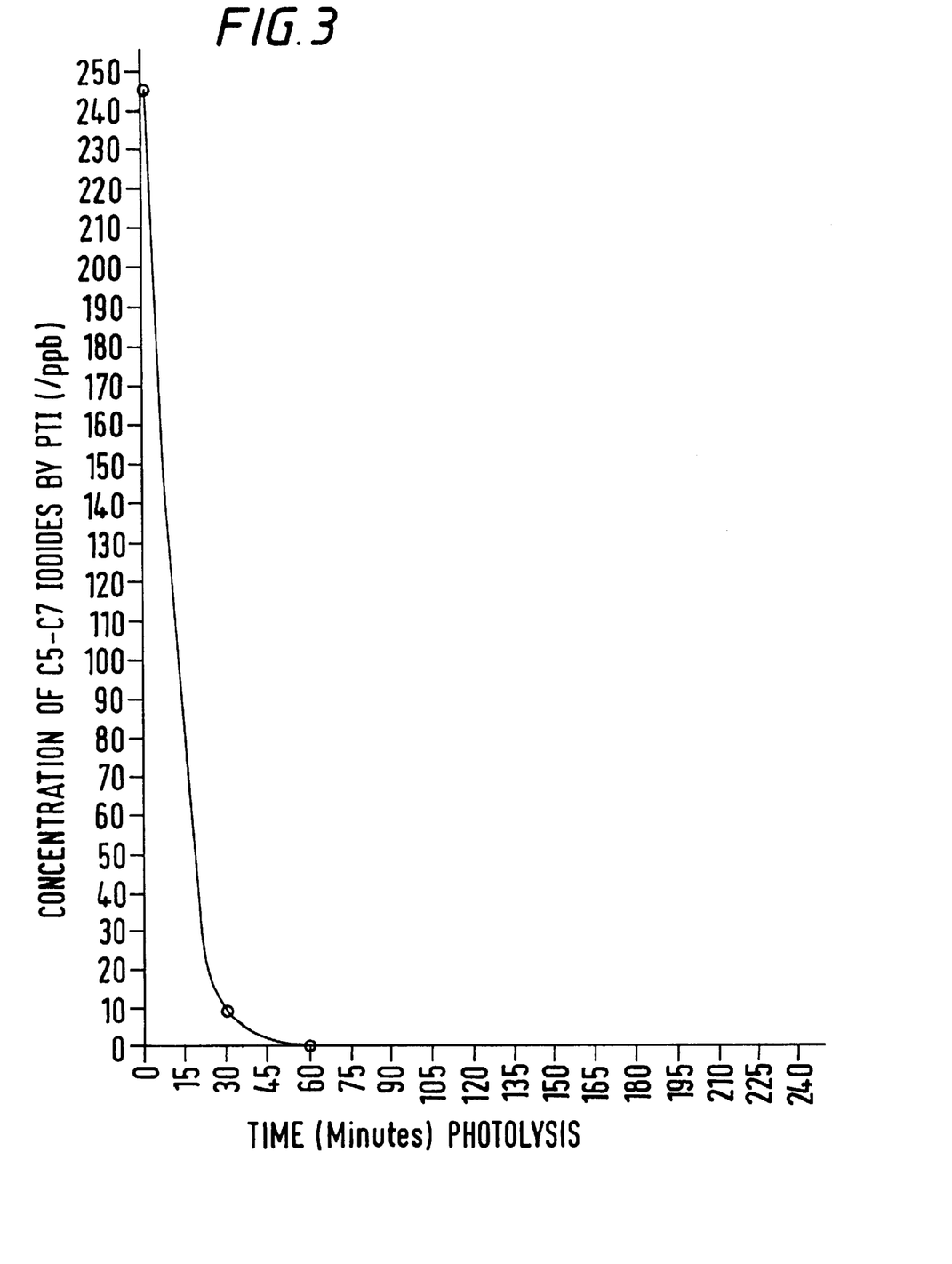
FIG. 3 is a graphical representation of the concentration of $C_5$ to $C_7$ organic iodides of Example 1.
Figure 4:
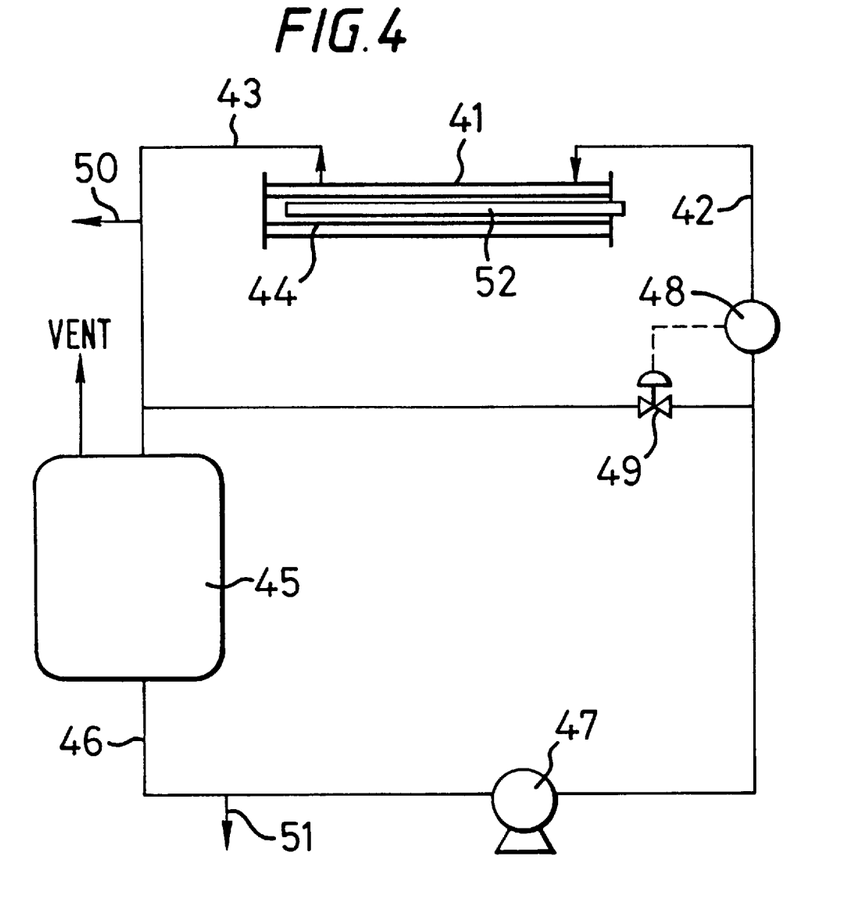
FIG. 4 is a diagrammatic representation of the apparatus used in Examples 4–20; and, FIGS. 5–9 are graphical representations of the results of Examples 4–17.
Figure 5:
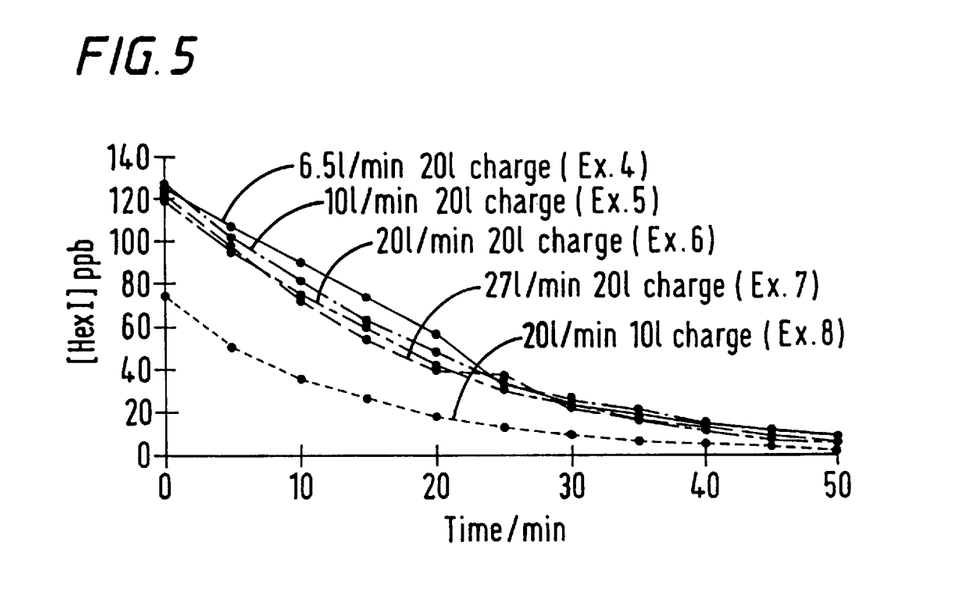
Figure 6:
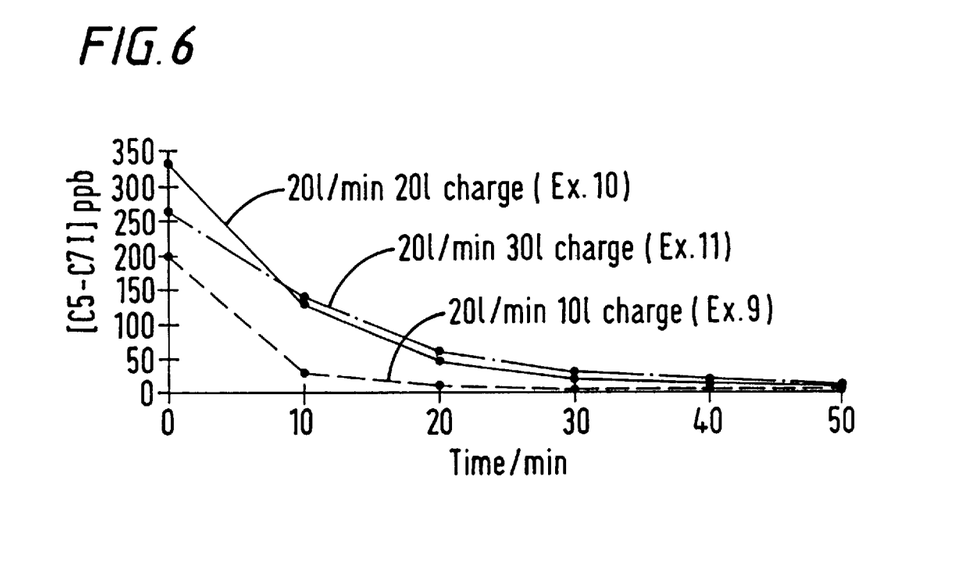
Figure 7:
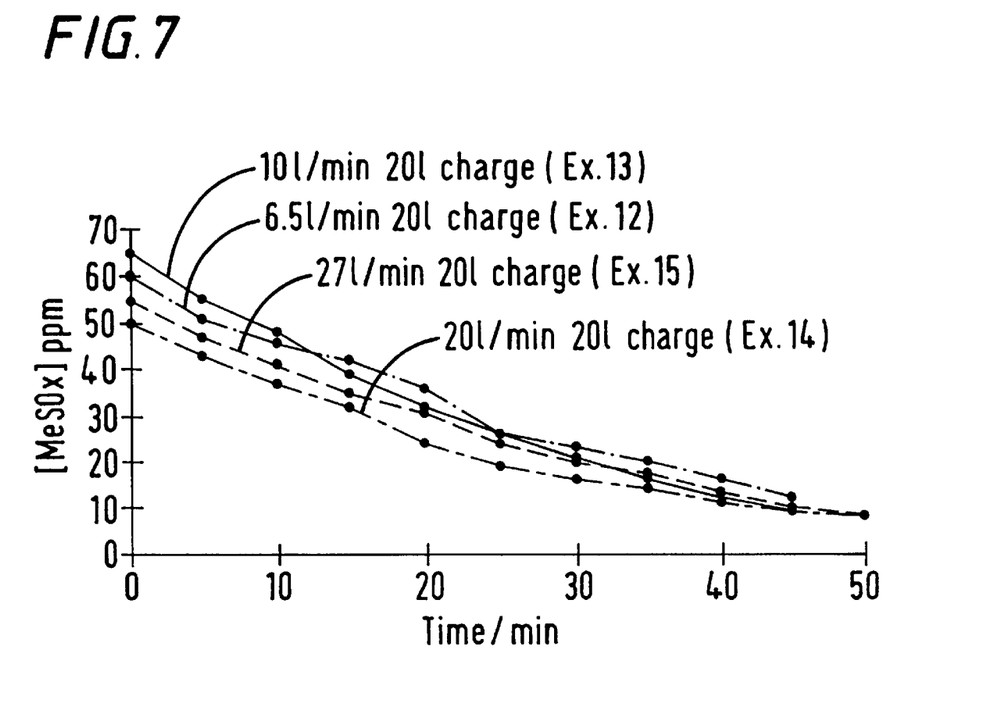
Figure 8:
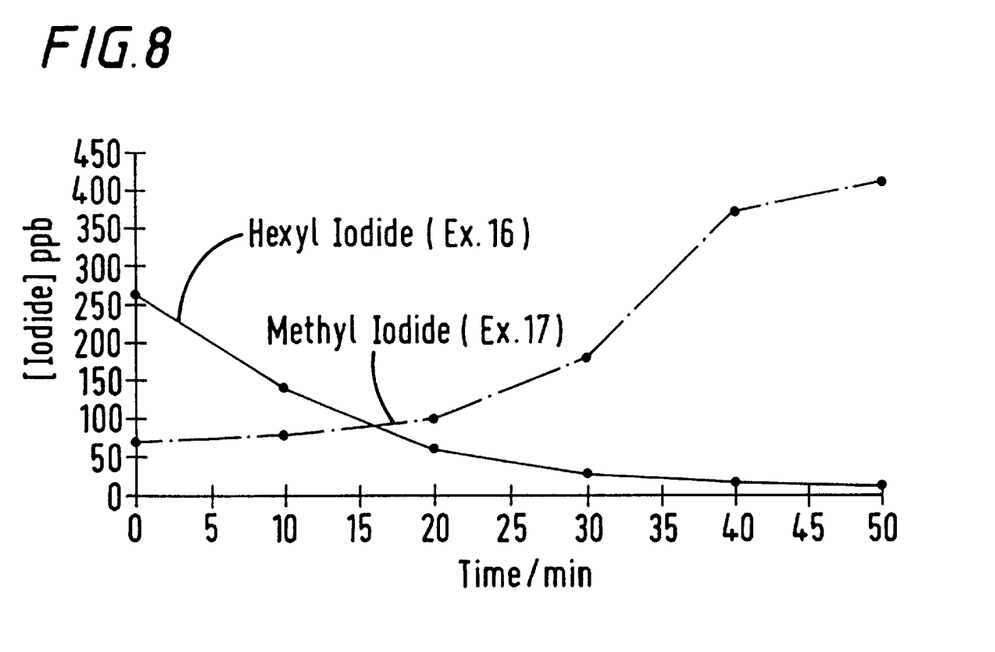
Figure 9:
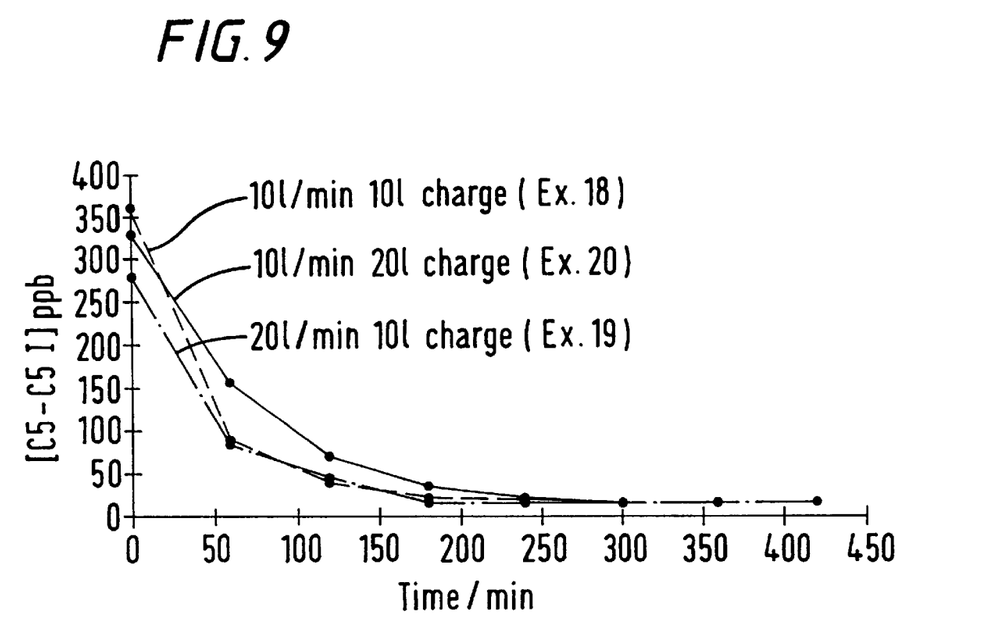

The invention will now be illustrated by means of the following examples and with reference to the Tables and Figures. FIGS. 1 and 4 are diagrams of apparatus used for exposing impure acetic acid to electromagnetic radiation. FIGS. 2 and 3 are graphs of impurity concentrations as a function time for Example 1. FIGS. 5 and 6 are graphs of the concentration of iodide impurities as a function of time for Examples 4 to 11. FIG. 7 is a graph of the concentration of mesityl oxide as a function of time for Examples 12 to 15. FIG. 8 is a graph of the concentration of iodide impurities and methyl iodide as a function of time for Examples 16 and 17. FIG. 9 is a graph of the concentration of iodide impurities as a function of time for Examples 18 to 20.

Referring to FIG. 1 which represents in diagrammatic form apparatus which was used to expose impure acetic acid to electromagnetic radiation.

In FIG. 1, a borosilicate glass reaction vessel (1) was provided with a 125 watt medium pressure UV mercury lamp (2) which in use, irradiated predominantly radiation of wavelength 365–366 nm with smaller amounts of radiation of wavelength 265, 297, 303, 313 and 334 nm and significant amounts in the visible region at 404–408, 436, 546 and 577–579 nm. The lamp had a power supply (3) and was positioned inside the reaction vessel (1) in a double-walled, quartz immersion well (4). The immersion well (4) was provided with a water inlet (5) and outlet (6). An optional nitrogen purge was available to the reaction vessel through inlet (7), passing out of the vessel through condenser (8) and bubbler trap (9). The reaction vessel was provided with a magnetic follower (15) turned by a magnetic stirrer (10). The reaction vessel also had an outlet tap (11) for taking samples and a stoppered inlet (12) for returning pre-runs from the sample point. The temperature of the reaction vessel was controlled in use by circulating water through the double-skinned immersion well (4) and thence to the condenser (8).

The apparatus shown in FIG. 1 was used to expose impure acetic acid to electromagnetic radiation. The acetic acid had been manufactured by the carbonylation of methanol and purified by distillation but still contained non-acidic and organic iodide impurities.

EXAMPLE 1

100 ml of impure acetic acid was charged to the reaction vessel and exposed to radiation from the mercury lamp without nitrogen purge. Water at ambient temperature (about 20° C.) was circulated through the immersion well (4) and condenser (8). 5 ml samples were withdrawn at intervals and analysed. The concentration of total non-acidics by PTI (purge and trap gas chromatography) is shown in the graph in FIG. 2 and the concentration of $C_5$ to $C_7$ organic iodides as measured by PTI is shown in the graph in FIG. 3. The non-acidics were dramatically reduced in about 90 minutes and the organic iodides were dramatically reduced in about 30 minutes. It is expected that purified acetic acid could be obtained from the treated acid by distillation.

EXAMPLE 2

Example 1 was repeated without withdrawal of samples. The acid was exposed to the radiation for 3 hours at 20° C.

At the end of this period the acid was flash distilled at atmospheric pressure and distillate fractions totalling up to 99% of the feed were combined and analysed. The results are shown in Table 1.

TABLE 1

|  | Impure Acetic Acid | Distilled Product |
| --- | --- | --- |
| Non Acidics | 100 ppm | 9 ppm |
| $C_5$–$C_7$ Iodides | 245 ppb | <1 ppb |
| Permanganate Time | <2 hrs | >8 hrs |

Permanganate times were measured at room temperature by adding 0.1 ml of 0.2M potassium permanganate solution to 2 ml of sample and 10 ml of distilled water; the permanganate time being the time required for the pink colour of the permanganate to be discharged. A permanganate time of greater than 2 hours was taken as a pass of the test.

EXAMPLE 3 AND COMPARATIVE EXPERIMENT A

A borosilicate sleeve was fitted to the immersion well to reduce significantly radiation having a wavelength below about 300 nm. Example 1 was repeated but at 77° C. for Example 3 and 45° C. for Comparative Experiment A; the temperature of the vessel being maintained by passing hot water through the immersion well (4) and condenser (8). Samples withdrawn at intervals were analysed for non-acidics by gas chromatography.

In Comparative Experiment A at 45° C. the concentration of non-acidics did not decrease over the time period of the experiment whereas in Example 3 at 77° C. there was a reduction after exposure. Therefore when a medium pressure mercury lamp fitted with a borosilicate filter to reduce significantly radiation having a wavelength of below about 300 nm was used in the process of the invention a temperature in excess of 45° C. was required for the non-acidics to be reduced.

Further experiments (Examples 4–20)

Further experiments illustrate step (a) of the present invention. It is expected that step (b) may be carried out by conventional methods such as distillation.

The apparatus used for the further experiments is shown in schematic form in FIG. 4. The apparatus comprised a UV cell (41) provided with inlet (42) and outlet (43) pipes for liquid and a quartz sleeve (44). A storage vessel (45) for liquid to be treated was connected by pipe (46) to pump (47). In use, liquid from the storage vessel (45) was pumped by pump (47) through the inlet (42) to the UV cell and returned through outlet (43) to the storage vessel (45). The flow rate of liquid from the storage vessel via the pump and through the UV cell was controlled by a flow rate transmitter (48) and by-pass valve (49). Sample points (50, 51) were provided for sampling the liquid before and after passage through the UV cell respectively. A UV lamp (52) was provided to irradiate the liquid in the UV cell.

The apparatus was used to expose acetic acid to electromagnetic radiation from both a medium pressure (1.3 kW) mercury lamp and a low pressure (30 W) mercury lamp, the latter irradiating predominantly radiation of wavelength 253.7 nm with a smaller amount of radiation at 150 nm. Desirably the clearance between the lamp (52) and the walls of the vessel (41) holding the acetic acid having halide impurities is as small as possible because of the poor transmissibility of UV radiation through acetic acid. The acetic acid had been manufactured by the carbonylation of a mixture of methanol and methyl acetate and had been purified by distillation. The acetic acid contained about 300 ppb $C_5$–$C_7$ iodide impurities and about 7 ppm mesityl oxide and was used either undosed or dosed (containing up to about 120 ppb hexyl iodide and about 60 ppm mesityl oxide). The acetic acid underwent multiple passes around the system. Samples were taken periodically and monitored for $C_5$–$C_7$ iodides, methyl iodide and mesityl oxide using gas chromatography. The experiments were carried out at an initial ambient temperature.

EXAMPLES 4–17

Table 2 shows results for Examples 4 to 17. In Examples 4 to 17 a 1.3 kW lamp was used. Results for Examples 4 to 8 are illustrated in FIG. 5. These demonstrate the effect of UV treatment on the concentration of hexyl iodide in the treated acid, using the 1.3 kW lamp and dosed feed, for varying volumes of acetic acid charged to the apparatus and for varying flow rates through the UV cell. Volume charges of 10 l and 20 l and flow rates varying between 6.5 and 27 l/min were used. Change in flow rate was observed to have no effect on the rate of conversion of hexyl iodide.

Results for Examples 9 to 11 are illustrated in FIG. 6. These demonstrate the effect of UV treatment on the concentration of $C_5$–$C_7$ iodides, using the 1.3 kW lamp and undosed feed, at a constant flow rate through the cell of 20 l/min and for volume charges of 10 l, 20 l and 30 l. For initial concentrations of $C_5$–$C_7$ iodides of 335, 265, and 200 ppb, a reduction to 11 ppb or less was observed in 50 minutes.

Results for Examples 12 to 15 are illustrated in FIG. 7. These demonstrate the effect of UV treatment on the concentration of mesityl oxide, using the 1.3 kW lamp and dosed feed, at a constant volume charge of 20 l and with flow rates through the cell varying between 6.5 l/min and 27 l/min. For initial concentrations of mesityl oxide of 50, 55, 60 and 65 ppm, a reduction to <10 ppm was observed in 50 minutes.

Results for Examples 16 and 17 are illustrated in FIG. 8. They demonstrate the effect $C_5$–$C_7$ iodide destruction had on methyl iodide production, using undosed feed. As the higher iodides were reduced in concentration there was a concomitant increase in methyl iodide concentration.

As the experiments for Examples 4 to 17 progressed the temperature of the stream steadily increased to about 80° C. in the first ten minutes and then levelled out. The oxidisable contaminants were reduced, however, this was not sufficient for the acetic acid samples to pass the permanganate time test. Permanganate times in the treated acid using dosed feed were in the range of 5 to 20 minutes (a pass is 120 minutes). Further increase in permanganate time might be expected following the separation step (b), which was not simulated in these experiments. The permanganate time for the dosed feed was less than 5 minutes.

TABLE 2

NATURE OF FEED (DOSED OR UNDOSED)

| Time/min | Dosed Ex. 4 6.5 l/min, 20l charge [Hex]* ppb | Dosed Ex. 5 10 l/min, 20l charge [Hex]* ppb | Dosed Ex. 6 20 l/min, 20l charge [Hex]* ppb | Dosed Ex. 7 27 l/min, 20l charge [Hex]* ppb | Dosed Ex. 8 20 l/min, 10l charge [Hex]* ppb | Undosed Ex. 9 20 l/min, 10l charge [C5–C7] ppb | Undosed Ex. 10 20 l/min, 20l charge [C5–C7] ppb | Undosed Ex. 10 20 l/min, 30l charge [C5–C7] ppb |
|---|---|---|---|---|---|---|---|---|
| 0 | 127 | 128 | 120 | 122 | 75 | 200 | 335 | 265 |
| 5 | 107 | 102 | 96 | 98 | 51 | | | |
| 10 | 91 | 82 | 76 | 73 | 36 | 31 | 130 | 140 |
| 15 | 74 | 63 | 60 | 54 | 27 | | | |
| 20 | 57 | 48 | 44 | 40 | 18 | 10 | 47 | 60 |
| 25 | 33 | 34 | 31 | 37 | 13 | | | |
| 30 | 26 | 24 | 23 | 22 | 9 | 6 | 20 | 28 |
| 35 | 21 | 16 | 19 | 16 | 6 | | | |
| 40 | 15 | 11 | 14 | 13 | 5 | 5 | 12 | 16 |
| 45 | 11 | 7 | 11 | 9 | 4 | | | |
| 50 | | 7 | 9 | 6 | 2 | 6 | 10 | 11 |

| Time/min | Dosed Ex. 12 6.5 l/min, 20l charge [MeSOx] ppm | Dosed Ex. 13 10 l/min, 20l charge [MeSOx] ppm | Dosed Ex. 14 20 l/min, 20l charge [MeSOx] ppm | Dosed Ex. 15 27 l/min, 20l charge [MeSOx] ppm | Undosed Ex. 16 [C5–C7] ppb | Undosed Ex. 17 [MeI] ppb |
|---|---|---|---|---|---|---|
| 0 | 60 | 55 | 50 | 65 | 265 | 70 |
| 5 | 51 | 47 | 43 | 55 | | |
| 10 | 46 | 41 | 37 | 48 | 140 | 80 |
| 15 | 42 | 35 | 32 | 39 | | |
| 20 | 36 | 31 | 24 | 32 | 60 | 100 |
| 25 | 26 | 24 | 19 | 26 | | |
| 30 | 23 | 20 | 16 | 21 | 28 | 220 |
| 35 | 20 | 17 | 14 | 16 | | |
| 40 | 16 | 13 | 11 | 12 | 16 | 370 |
| 45 | 12 | 10 | 9 | 9 | | |
| 50 | | 8 | 8 | 8 | 11 | 410 |

*'Hex' is an abbreviation for hexyl iodide

EXAMPLES 18–20

Results for Examples 18 to 20 using undosed feed are given in Table 3 and are illustrated in FIG. 9. They demonstrate the effect of UV treatment on the concentrations of $C_5$–$C_7$ iodides, using a 30 W lamp and undosed feed. The flow rates through the cell were varied between 10 and 20 l/min and the volume charge was varied between 10 and 20 l. $C_5$–$C_7$ iodides were reduced from about 300 ppb to 14 pbb in 300 minutes. In the undosed experiments mesityl oxide was reduced from about 6 ppm to <2 ppm in 90 minutes. However, as with the 1.3 kW lamp, the total reduction in non-acidics was not sufficient for the acetic acid to pass the permanganate time test. For the undosed experiments the permanganate time of the product reached 60 minutes after 300 minutes. The permanganate time of the undosed feed was 25 minutes, indicating that a significant improvement had been made. As in the 1.3 kW lamp case the rate of removal of contaminants was independent of flow rate through the cell (10 to 20 l/min). The temperature of the stream steadily increased with time to a maximum value of about 50° C.

Examples 4 to 20 show that UV radiation can be used to reduce both higher organic iodides and non-acidics from acetic acid. Under the conditions mentioned above higher organic iodides can be reduced to <10 ppb. However, the reduction in non-acidics achieved was not sufficient for the samples to pass the permanganate test.

Methyl iodide is produced in the process and it is expected that this may be removed by distillation.

TABLE 3

| Time [min] | Example 18 10 l/min, 10 l charge [C5–C7] ppb | Example 19 20 l/min, 10 l charge [C5–C7] ppb | Example 20 10 l/min, 20 l charge [C5–C7] ppb |
|---|---|---|---|
| 0 | 360 | 280 | 330 |
| 60 | 90 | 85 | 155 |
| 120 | 40 | 45 | 70 |
| 180 | 22 | 16 | 35 |
| 240 | 18 | 15 | 21 |
| 300 | 14 | 15 | 14 |
| 360 | | 15 | |
| 420 | | 15 | |

I claim:

1. A process for the purification of a $C_2$ to $C_4$ carboxylic acid, a $C_2$ to $C_4$ anhydride, or a mixture thereof having halide impurities, which process comprises the steps of (a) exposing the impure acid, anhydride or mixture thereof to electromagnetic radiation under conditions of intensity, wavelength and temperature to convert at least a portion of the halide impurities to lower boiling halide components, higher boiling halide components or mixtures thereof and (b) separating the halide components formed in step (a) from the $C_2$ to $C_4$ carboxylic acid, anhydride or mixture thereof.

2. A process according to claim 1 wherein the $C_2$ to $C_4$ carboxylic acid is acetic acid.

3. A process according to claim 1 wherein the halide impurities are iodine-containing compounds.

4. A process according to claim 3 wherein the iodine-containing compounds are organic $C_5$ to $C_7$ iodides.

5. A process according to claim 1 wherein the impure acid, anhydride or mixture thereof is exposed to the electromagnetic radiation at a temperature in the range from 20° to 85° C.

6. A process according to claim 1 wherein the electromagnetic radiation has a source which is at least one medium pressure or low pressure mercury lamp emitting radiation predominantly in the wavelength ranges 300 to 370 nm and 254 nm respectively.

7. A process according to claim 1 wherein the halide components formed in step (a) are separated from the $C_2$ to $C_4$ carboxylic acid, anhydride or mixture thereof by distillation.

8. A process according to claim 1 wherein the exposure step (a) and the separation step (b) are performed sequentially by exposing the impure acid, anhydride or mixture thereof in a separate vessel prior to distillative separation.

9. A process for the purification of a $C_2$ to $C_4$ carboxylic acid, a $C_2$ to $C_4$ anhydride, or mixture thereof prepared by a carbonylation process, the acid, anhydride or mixture thereof having non-halide, non-acidic, non-anhydride impurities or mixtures thereof comprising $C_1$ to $C_6$ esters, mesityl oxide or mixtures thereof, which process comprises the steps of (a) exposing the impure acid, anhydride or mixture thereof to electromagnetic radiation under conditions of intensity, wavelength and temperature, to convert at least a portion of the impurities to a lower boiling component, a higher boiling component or mixtures thereof and (b) separating the components formed in step (a) from the $C_2$ to $C_4$ carboxylic acid, anhydride or mixture thereof.

10. A process according to claim 9 wherein step (b) the components formed in step (a) are separated from the $C_2$ to $C_4$ carboxylic acid, anhydride or mixture thereof by distillation.

11. A process according to claim 9 wherein the exposure step (a) and the separation step (b) are performed sequentially by exposing the impure acid, anhydride or mixtures thereof in a separate vessel prior to distillative separation.

12. A process for the purification of a $C_2$ to $C_4$ carboxylic acid, a $C_2$ to $C_4$ anhydride or mixture thereof having $C_5$ to $C_7$ iodide impurities, which process comprises the steps of (a) exposing the impure acid, anhydride or mixture thereof to electromagnetic radiation under conditions of intensity, wavelength and temperature, to convert at least a portion of the $C_5$ to $C_7$ iodide impurities to methyl iodide and (b) separating the methyl iodide formed in step (a) from the $C_2$ to $C_4$ carboxylic acid, anhydride or mixture thereof.

13. A process for increasing the permanganate time of acetic acid having halide impurities and non-halide, non-acidic, non-anhydride impurities and mixtures thereof which process comprises exposing the acetic acid to electromagnetic radiation under conditions of intensity, wavelength and temperature to convert at least a portion of the halide impurities to a lower boiling halide component, a higher boiling halide component and mixtures of the halide components and at least a portion of the non-halide, non-acidic, non-anhydride impurities or mixtures thereof to lower boiling components and higher boiling components.

14. A process according to claim 13, wherein the halide components and the non-halide, non-acidic, non-anhydride components or mixtures thereof are separated from the acetic acid.

\* \* \* \* \*